(12) United States Patent
Reynolds

(10) Patent No.: US 6,448,374 B1
(45) Date of Patent: Sep. 10, 2002

(54) PRODUCTION OF PHOSPHOPEPTIDES FROM CASEIN

(75) Inventor: Eric Charles Reynolds, Melbourne (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 08/137,086

(22) PCT Filed: Apr. 16, 1992

(86) PCT No.: PCT/AU92/00175

§ 371 (c)(1),
(2), (4) Date: Mar. 4, 1994

(87) PCT Pub. No.: WO92/18526

PCT Pub. Date: Oct. 29, 1992

(30) Foreign Application Priority Data

Apr. 19, 1991 (AU) .............................................. PK5706

(51) Int. Cl.⁷ .............................. C07K 1/14; C07K 1/30
(52) U.S. Cl. ...................... 530/324; 530/325; 530/326; 530/352; 530/412; 530/417; 530/418; 530/420; 435/68.1
(58) Field of Search ................................. 530/326, 325, 530/324, 352, 412, 418, 420, 417; 435/68.1

(56) References Cited

U.S. PATENT DOCUMENTS

| | | | | |
|---|---|---|---|---|
| 4,358,465 A | * | 11/1982 | Brule et al. | 426/42 |
| 4,740,462 A | * | 4/1988 | Brule et al. | 435/69 |
| 4,816,398 A | * | 3/1989 | Brule et al. | 435/69 |
| 4,933,173 A | * | 6/1990 | Bristow et al. | 424/54 |
| 5,227,154 A | | 7/1993 | Reynolds | |

* cited by examiner

*Primary Examiner*—Christopher S. F. Low
*Assistant Examiner*—Anish Gupta
(74) *Attorney, Agent, or Firm*—Foley & Lardner

(57) ABSTRACT

A method for the preparation of selected phosphopeptides having anticariogenic and other activities, comprising the steps of completely digesting a soluble monovalent cation salt of casein in solution with a proteolytic enzyme, adding a mineral acid to the solution to adjust the pH to about 4.7, removing any precipitate produced, adding $CaCl_2$ to a level of about 1.0% w/v to cause aggregation of at least the selected phosphopeptides in said digested solution, separating the aggregated phosphopeptides from the solution through a filter having a molecular weight exclusion limit lying substantially within the range 10,000 to 20,000 while passing the bulk of the remaining phosphopeptides and solution, diafiltering the separated phosphopeptides with water through a filter and concentrating and drying the retentate.

18 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 25
      (B) TYPE: Amino acid
      (C) STRANDEDNESS: single
      (D) TOPOLOGY: linear (ii) MOLECULE TYPE: Protein (ix) FEATURE:
      (A) NAME/KEY: Phosphoserine
      (B) LOCATION: 15
      (D) OTHER INFORMATION:
         Post-translationally phosphorylated serine (ix) FEATURE:
      (A) NAME/KEY: Phosphoserine
      (B) LOCATION: 17
      (D) OTHER INFORMATION:
         Post-translationally phosphorylated serine

```
    (ix) FEATURE:
         (A) NAME/KEY: Phosphoserine
         (B) LOCATION: 18
         (D) OTHER INFORMATION:
             Post-translationally phosphorylated serine (ix) FEATURE:
         (A) NAME/KEY: Phosphoserine
         (B) LOCATION: 19
         (D) OTHER INFORMATION:
             Post-translationally phosphorylated serine (xi) SEQUENCE DESCRIPTION: SEQ ID NO:1:

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

(2) INFORMATION FOR SEQ ID NO:2:

(i) SEQUENCE CHARACTERISTICS:
        (A) LENGTH: 21
        (B) TYPE:   Amino acid
        (C) STRANDEDNESS: single
        (D) TOPOLOGY: linear (ii) MOLECULE TYPE:   Protein (ix) FEATURE:
         (A) NAME/KEY: Pyroglutamate
         (B) LOCATION: 1
         (D) OTHER INFORMATION:
             A certain amount will exist in this form (ix) FEATURE:
         (A) NAME/KEY: Phosphoserine
         (B) LOCATION: 6
         (D) OTHER INFORMATION:
             Post-translationally phosphorylated serine (ix) FEATURE:
         (A) NAME/KEY: Phosphoserine
         (B) LOCATION: 8
         (D) OTHER INFORMATION:
             Post-translationally phosphorylated serine (ix) FEATURE:
         (A) NAME/KEY: Phosphoserine
         (B) LOCATION: 9
         (D) OTHER INFORMATION:
             Post-translationally phosphorylated serine (ix) FEATURE:
         (A) NAME/KEY: Phosphoserine
         (B) LOCATION: 10
         (D) OTHER INFORMATION:
             Post-translationally phosphorylated serine (ix) FEATURE:
         (A) NAME/KEY: Phosphoserine
         (B) LOCATION: 17
         (D) OTHER INFORMATION:
             Post-translationally phosphorylated serine (xi) SEQUENCE DESCRIPTION: SEQ ID NO:2:

Gln Met Glu Ala Glu Ser Ile Ser Ser Ser Glu Glu Ile Val Pro Asn
1               5                   10                  15

Ser Val Glu Gln Lys
            20
```

(2) INFORMATION FOR SEQ ID NO:3:

(i) SEQUENCE CHARACTERISTICS:
        (A) LENGTH: 24
        (B) TYPE: Amino acid
        (C) STRANDEDNESS: single
        (D) TOPOLOGY: linear (ii) MOLECULE TYPE: Protein (ix) FEATURE:
        (A) NAME/KEY: Phosphoserine
        (B) LOCATION: 14
        (D) OTHER INFORMATION:
            Post-translationally phosphorylated serine (ix) FEATURE:
        (A) NAME/KEY: Phosphoserine
        (B) LOCATION: 16
        (D) OTHER INFORMATION:
            Post-translationally phosphorylated serine (ix) FEATURE:
        (A) NAME/KEY: Phosphoserine
        (B) LOCATION: 17
        (D) OTHER INFORMATION:
            Post-translationally phosphorylated serine (ix) FEATURE:
        (A) NAME/KEY: Phosphoserine
        (B) LOCATION: 18
        (D) OTHER INFORMATION:
            Post-translationally phosphorylated serine (xi) SEQUENCE DESCRIPTION: SEQ ID NO:3:

```
Glu Leu Glu Glu Leu Asn Val Pro Gly Glu Ile Val Glu Ser Leu Ser
 1               5                  10                  15

Ser Ser Glu Glu Ser Ile Thr Arg
            20
```

(2) INFORMATION FOR SEQ ID NO:4:

(i) SEQUENCE CHARACTERISTICS:
        (A) LENGTH: 25
        (B) TYPE: Amino acid
        (C) STRANDEDNESS: single
        (D) TOPOLOGY: linear (ii) MOLECULE TYPE: Protein (ix) FEATURE:
        (A) NAME/KEY: Phosphoserine
        (B) LOCATION: 11
        (D) OTHER INFORMATION:
            Post-translationally phosphorylated serine (ix) FEATURE:
        (A) NAME/KEY: Phosphoserine
        (B) LOCATION: 12
        (D) OTHER INFORMATION:
            Post-translationally phosphorylated serine (ix) FEATURE:
        (A) NAME/KEY: Phosphoserine
        (B) LOCATION: 13
        (D) OTHER INFORMATION:
            Post-translationally phosphorylated serine (ix) FEATURE:
        (A) NAME/KEY: Phosphoserine
        (B) LOCATION: 16
        (D) OTHER INFORMATION:
            Post-translationally phosphorylated serine (xi) SEQUENCE DESCRIPTION: SEQ ID NO:4:

Asn Ala Asn Glu Glu Glu Tyr Ser Ile Gly Ser Ser Ser Glu Glu Ser
1               5                   10                  15

Ala Glu Val Ala Thr Glu Glu Val Lys
            20                  25

(2) INFORMATION FOR SEQ ID NO:5:

(i) SEQUENCE CHARACTERISTICS:
        (A) LENGTH: 21
        (B) TYPE: Amino acid
        (C) STRANDEDNESS: single
        (D) TOPOLOGY: linear (ii) MOLECULE TYPE:  Protein (ix) FEATURE:
        (A) NAME/KEY: Phosphoserine
        (B) LOCATION: 6
        (D) OTHER INFORMATION:
            Post-translationally phosphorylated serine (ix) FEATURE:
        (A) NAME/KEY: Phosphoserine
        (B) LOCATION: 8
        (D) OTHER INFORMATION:
            Post-translationally phosphorylated serine (ix) FEATURE:
        (A) NAME/KEY: Phosphoserine
        (B) LOCATION: 9
        (D) OTHER INFORMATION:
            Post-translationally phosphorylated serine (ix) FEATURE:
        (A) NAME/KEY: Phosphoserine
        (B) LOCATION: 10
        (D) OTHER INFORMATION:
            Post-translationally phosphorylated serine (ix) FEATURE:
        (A) NAME/KEY: Phosphoserine
        (B) LOCATION: 17
        (D) OTHER INFORMATION:
            Post-translationally phosphorylated serine (xi) SEQUENCE DESCRIPTION: SEQ ID NO:5:

Gln Met Glu Ala Glu Ser Ile Ser Ser Ser Glu Glu Ile Val Pro Asp
1               5                   10                  15

Ser Val Glu Gln Lys
            20

(2) INFORMATION FOR SEQ ID NO:6:

(i) SEQUENCE CHARACTERISTICS:
        (A) LENGTH: 21
        (B) TYPE: Amino acid
        (C) STRANDEDNESS: single
        (D) TOPOLOGY: linear (ii) MOLECULE TYPE:  Protein (ix) FEATURE:
        (A) NAME/KEY: Phosphoserine
        (B) LOCATION: 6
        (D) OTHER INFORMATION:
            Post-translationally phosphorylated serine (ix) FEATURE:
        (a) NAME/KEY: Phosphoserine
        (b) LOCATION: 8
        (d) OTHER INFORMATION:
            Post-translationally phosphorylated serine (ix) FEATURE:
            (a) NAME/KEY: Phosphoserine
            (b) LOCATION: 9
            (d) OTHER INFORMATION:
                Post-translationally phosphorylated serine (ix) FEATURE:
            (a) NAME/KEY: Phosphoserine
            (b) LOCATION: 10
            (d) OTHER INFORMATION:
                Post-translationally phosphorylated serine (ix) FEATURE:
            (a) NAME/KEY: Phosphoserine
            (b) LOCATION: 17
            (d) OTHER INFORMATION:
                Post-translationally phosphorylated serine (xi) SEQUENCE DESCRIPTION: SEQ ID NO:6:

Gln Met Glu Ala Glu Ser Ile Ser Ser Ser Glu Glu Ile Val Pro Asp
1               5                  10                  15

Ser Val Glu Glu Lys
            20

(2) INFORMATION FOR SEQ ID NO:7:

(i) SEQUENCE CHARACTERISTICS:
            (A) LENGTH: 20
            (B) TYPE: Amino acid
            (C) STRANDEDNESS: single
            (D) TOPOLOGY: linear (ii) MOLECULE TYPE:  Protein (ix) FEATURE:
            (a) NAME/KEY: Phosphoserine
            (b) LOCATION: 7
            (d) OTHER INFORMATION:
                Post-translationally phosphorylated serine (ix) FEATURE:
            (a) NAME/KEY: Phosphoserine
            (b) LOCATION: 8
            (d) OTHER INFORMATION:
                Post-translationally phosphorylated serine (ix) FEATURE:
            (a) NAME/KEY: Phosphoserine
            (b) LOCATION: 9
            (d) OTHER INFORMATION:
                Post-translationally phosphorylated serine (ix) FEATURE:
            (a) NAME/KEY: Phosphoserine
            (b) LOCATION: 15
            (d) OTHER INFORMATION:
                Post-translationally phosphorylated serine (xi) SEQUENCE DESCRIPTION: SEQ ID NO:7:

Asn Thr Met Glu His Val Ser Ser Ser Glu Glu Ser Ile Ile Ser Gln
1               5                  10                  15

Glu Thr Tyr Lys
            20

(2) INFORMATION FOR SEQ ID NO:8:

(i) SEQUENCE CHARACTERISTICS:
            (A) LENGTH: 21
            (B) TYPE: Amino acid
            (C) STRANDEDNESS: single
            (D) TOPOLOGY: linear (ii) MOLECULE TYPE:  Protein

```
        (ix) FEATURE:
              (a) NAME/KEY: Phosphoserine
              (b) LOCATION: 8
              (d) OTHER INFORMATION:
                   Post-translationally phosphorylated serine (ix) FEATURE:
              (a) NAME/KEY: Phosphoserine
              (b) LOCATION: 9
              (d) OTHER INFORMATION:
                   Post-translationally phosphorylated serine (ix) FEATURE:
              (a) NAME/KEY: Phosphoserine
              (b) LOCATION: 10
              (d) OTHER INFORMATION:
                   Post-translationally phosphorylated serine (ix) FEATURE:
              (a) NAME/KEY: Phosphoserine
              (b) LOCATION: 16
              (d) OTHER INFORMATION:
                   Post-translationally phosphorylated serine (xi) SEQUENCE DESCRIPTION: SEQ ID NO:8:

Lys Asn Thr Met Glu His Val Ser Ser Ser Glu Glu Ser Ile Ile Ser
 1               5                  10                  15

Gln Glu Thr Tyr Lys
             20

(2) INFORMATION FOR SEQ ID NO:9:

(i) SEQUENCE CHARACTERISTICS:
             (A) LENGTH: 37
             (B) TYPE: Amino acid
             (C) STRANDEDNESS: single
             (D) TOPOLOGY: linear (ii) MOLECULE TYPE:  Protein (ix) FEATURE:
             (A) NAME/KEY: Phosphoserine
             (B) LOCATION: 4
             (D) OTHER INFORMATION:
                   Post-translationally phosphorylated serine (ix) FEATURE:
             (A) NAME/KEY: Phosphoserine
             (B) LOCATION: 6
             (D) OTHER INFORMATION:
                   Post-translationally phosphorylated serine (ix) FEATURE:
             (A) NAME/KEY: Phosphoserine
             (B) LOCATION: 22
             (D) OTHER INFORMATION:
                   Post-translationally phosphorylated serine (ix) FEATURE:
             (A) NAME/KEY: Phosphoserine
             (B) LOCATION: 24
             (D) OTHER INFORMATION:
                   Post-translationally phosphorylated serine (ix) FEATURE:
             (A) NAME/KEY: Phosphoserine
             (B) LOCATION: 25
             (D) OTHER INFORMATION:
                   Post-translationally phosphorylated serine (ix) FEATURE:
             (A) NAME/KEY: Phosphoserine
             (B) LOCATION: 26
             (D) OTHER INFORMATION:
                   Post-translationally phosphorylated serine
```

```
-continued (ix) FEATURE:
        (A) NAME/KEY: Phosphoserine
        (B) LOCATION: 33
        (D) OTHER INFORMATION:
             Post-translationally phosphorylated serine (xi) SEQUENCE DESCRIPTION: SEQ ID NO:9:

Asp Ile Gly Ser Glu Ser Thr Glu Asp Gln Ala Met Glu Asp Ile Lys
1               5                   10                  15

Gln Met Glu Ala Glu Ser Ile Ser Ser Ser Glu Glu Ile Val Pro Asn
                20              25              30

Ser Val Glu Gln Lys
            35
```

PRODUCTION OF PHOSPHOPEPTIDES FROM CASEIN

FIELD OF THE INVENTION

This invention relates to the production of phosphopeptides having anticariogenic and other properties from casein.

BACKGROUND OF THE INVENTION

In our Australian Patent No. 593365, we have described that four of the many phosphopeptides released by tryptic digestion of casein have anticariogenic (tooth-decay-inhibiting) activity. These peptides all contain the active sequence -Ser(P)-Ser(P)-Ser(P)-Glu-Glu- and correspond to $\alpha_{s1}$ (59–79) SEQ.ID No 2 ($T_1$), $\beta$(2–25) SEQ.ID No 3 ($T_2$), $\alpha_{s2}$(46–70) SEQ.ID No 4 ($T_4$) and $\alpha_{s2}$(2–21) SEQ.ID No 7 ($T_3$). The methods described for the production of the anticariogenic phosphopeptides are selective precipitation and ion exchange chromatography. While these methods produce very pure preparations of these peptides, they have not received general acceptance in the dairy industry due to their cost and the level of technical skill required.

Recently membrane ultrafiltration has found broad acceptance in the dairy industry for milk treatment. In U.S. Pat. Nos. 4,358,465, 4,361,587 and 4,495,176, Brule et al describe an ultrafiltration method for the production of casein phosphopeptides as dietetic aliments. This procedure proves unsuitable for the production of anticariogenic phosphopeptides due to the predominance of non-anticariogenic phosphopeptides in the preparations.

In AU-B 66783/81 and 51491/85 Brule et al, a method of extracting phosphopeptides for use as nutritional complements is disclosed in which an aggregate forming bivalent cation is used in combination with ultrafiltration followed by diafiltration with water to extract the desired phosphopeptides selected for the above purpose. This procedure is similarly unsuitable for the production of anticariogenic phosphopeptides since diafiltration with water results in the deaggregation of the anticariogenic phosphopeptides.

SUMMARY OF THE INVENTION AND OBJECT

It is an object of the present invention to provide a method of preparing selected phosphopeptides from casein using ultrafiltration.

The invention provides a method for the preparation of selected phosphopeptides comprising the steps of completely digesting a soluble monovalent cation salt of casein in solution, introducing a di or trivalent metal ion to cause aggregation of at least the selected phosphopeptides in said digested solution, and diafiltering the solution containing the aggregation ion through a filter having a molecular weight exclusion limit selected to retain at least said aggregated phosphopeptides while passing the bulk of the remaining phosphopeptides and non-phosphorylated peptides.

In the methods described by Brule et al, the object is to obtain a broad range of phosphopeptides from casein for use as a dietetic aliment. Therefore Brule et al do not each that the hydrolysed casein compound must be diafiltrated in the presence of the aggregating ion to ensure that the selected phosphopeptides are filtered from the solution while allowing the remaining phosphopeptides and non-phosphorylated peptides to pass during the diafiltration process. This represents a significant advance in the art since it enables the use of an industry accepted method of extraction which results in a preparation which is rich (>90% w/w) in the desired phosphopeptides.

In a preferred form of the invention, the selected phosphopeptides are the anticariogenic phosphopeptides referred to above, and the molecular exclusion limit adopted during the filtering step of the above method preferably substantially falls within the range 10,000 to 20,000.

The soluble monovalent cation salt of casein, such as sodium caseinate or potassium caseinate, may be present in the solution in a concentration substantially falling within the range 0.1 to 50% w/w, which is preferably digested using a proteolytic enzyme, such as pancreatin, trypsin, papain or chymotrypsin, or a mixture of proteolytic enzymes such as trypsin and chymotrypsin or by chemical means, such as cyanogen bromide. The enzyme(s) to casein ratio can range from about 1:1000 to 1:10 (w:w) but this would be selected to allow complete digestion of the casein as defined above. The pH of the hydrolysis should preferably be controlled at optimum for the enzymes to allow complete casein digestion. The temperature also should be optimised for complete digestion but temperature induced degradation (deamidation, dephosphorylation and peptidolysis) should be minimised. The optimal temperature is between about 20° C. and 60° C.

In a preferred form of the invention, after digestion HCl is added at room temperature to about pH 4.7 and any precipitate (this should be minimal) removed. $CaCl_2$ is then added to the supernatant to a level of about 1.0% w/v. Phosphopeptides in the presence of 1.0% w/v calcium (II) aggregate. The anticariogenic phosphopeptides (ie. containing the sequence -Ser(P)-Ser(P)-Ser(P)-Glu-Glu-) form hexamers which are separated from the smaller non-anticariogenic phosphopeptide aggregates by extensive diafiltration through a 10,000 molecular weight exclusion limit filter with a $CaCl_2$ solution preferably 1.0% w/v. The preferred molecular weight exclusion limit of the membrane filter should not be less than 10,000 or greater than about 20,000. The addition of a $CaCl_2$ solution, or some other suitable di/trivalent metal ion, such as zinc (II) or ferric (III), is essential for diafiltration in order to maintain the integrity of the anticariogenic phosphopeptide aggregates thus allowing separation of the anticariogenic from the non-anticariogenic phosphopeptides.

After several volumes of 1.0% $CaCl_2$ w/v have passed through the membrane filter to achieve greater than 90% purity of the anticariogenic phosphopeptides the ultraretentate containing the anticariogenic phosphopeptides can be diafiltered with water through a 1,000 molecular weight exclusion limit filter to remove calcium if desired. The retentate is then concentrated and spray dried.

The calcium, zinc and ferric salts of the anticariogenic phosphopeptide preparation (ACPP) can be converted to a sodium salt by acidifying a 10% w/v solution of the calcium ACPP to a low pH, circa pH 2.0, with HCl. After extensive diafiltration through a 1,000 molecular weight exclusion limit filter the retentate is neutralised to pH 7.0 with NaOH and then diafiltered with water through the same filter to remove excess sodium chloride.

The calcium ACPP can be converted to calcium phosphate ACPP by addition of $CaCl_2$ and $Na_2HPO_4$ where the Ca/P final ratio is 1.67. The peptide $\alpha_{s1}$(59–79) can bind 21 Ca and 13 $PO_4$. The filtrate of the above process is suited for the purification of other bioactive casein peptides by size and charge-based separation technologies and can be used as microbiological growth media, as dietary supplements after debittering or as a nitrogen fertilizer.

A presently preferred embodiment of the invention will now be described with reference to the following example.

EXAMPLE

Sodium caseinate was prepared by acidifying milk with 0.1 M HCl to pH 4.7 and neutralising the precipitate with NaOH to pH 7.0. A 10% w/v solution of sodium caseinate was prepared and adjusted to pH 8.0. Trypsin (Novo) was added to 0.2% w/v and the hydrolysis allowed to proceed to completion at 50° C. with adjustment to pH 8.0 by constant addition of NaOH. The pH of the solution was then adjusted to pH 4.7 with 5 M HCl and the precipitate removed at room temperature by centrifugation. The supernatant was microfiltered through an 8 micron filter, and then adjusted to pH 7.0 with NaOH and $CaCl_2$ added to a level of 1.0% w/v. This solution was then diafiltered through an Amicon YM10 (10,000 molecular weight exclusion limit) with 3 to 5 volumes of 1.0% w/v $CaCl_2$. The retentate was then washed with 1 volume of distilled/deionised water through an Amicon YM1 filter (1,000 molecular weight exclusion limit). The individual peptides of this preparation were separated by ion exchange FPLC and reverse phase HPLC as described in the aforementioned patent and identified by amino acid composition and sequence analyses after conversion of the Ser(P) residues to S-ethyl cysteine. An analysis of the preparation is shown in Table 1.

TABLE 1

Composition of an Anticariogenic Phosphopeptide Preparation

| Peptide | % w/w |
|---|---|
| $\alpha_{s2}$(1–21) (SEQ. ID No 8) | 0.8 |
| $\beta$(1–25) (SEQ. ID No 1) | 22.3 |
| $\alpha_{s2}$(2–21) (SEQ. ID No 7) ($T_3$) | 5.7 |
| $\beta$(2–25) (SEQ. ID No 3) ($T_2$) | 17.9 |
| $\alpha_{s1}$(59–79) (SEQ. ID No 2) ($T_1$) | 21.4 |
| Desamido$^{74}\alpha_{s1}$(59–79) (SEQ. ID No 5) | 6.3 |
| $\alpha_{s2}$(46–70) (SEQ. ID No 4) ($T_4$) | 6.8 |
| Desamido$^{74,78}\alpha_{s1}$(59–79) (SEQ. ID No 6) | 6.4 |

TABLE 1-continued

Composition of an Anticariogenic Phosphopeptide Preparation

| Peptide | % w/w |
|---|---|
| $\alpha_{s1}$(43–79) (SEQ. ID No 9) | 3.3 |
| NAP* | 9.1 |

*NAP = non-anticariogenic peptides

This preparation contains the four anticariogenic phosphopeptides described in the aforementioned patent, [$\beta$(2–25), $T_2$, $\alpha_{s1}$(59–79), $T_1$, $\alpha_{s2}$(2–21), $T_3$ and $\alpha_{s2}$(46–70), $T_4$], those related peptides incompletely hydrolysed by trypsin [$\alpha_{s2}$(1–21), $\beta$(1–25) and $\alpha_{s1}$(43–79)] and also minor levels of the two deamidated forms of $\alpha_{s1}$(59–79), desamido$^{74}$ and desamido$^{74,78}$ which result from temperature induced deamidation, this occurs in an even greater extent in commercial production of sodium caseinate due to higher temperatures and extremes of pH, although the presence of the deamidated forms has no effect on anticariogenic activity. The anticariogenic phosphopeptides were 90.9% w/w of the peptides produced.

If pure $\alpha_{s1}$-casein is used in place of casein then $\alpha_{s1}$(59–79) will be obtained by this process with minor amounts of the deamidated forms of this peptide depending on hydrolysis conditions. If pure $\beta$-casein is used then only $\beta$(1–25) and $\beta$(2–25) will be obtained using this process.

When crude enzymes are used (such as pancreatin), slight truncation (both N- and C-terminally) of the nine listed phosphopeptides can occur. As long as this truncation is only slight, there is no loss of activity. In fact, pancreatin produces a preparation with slightly greater specific activity on a weight basis when compared with purified trypsin.

The sequences of the nine peptides, which include the peptides $T_1$ to $T_4$ of the aforementioned patent, and the other peptides referred to above are detailed in the following sequence listing

What is claimed is:

1. A method for the preparation of selected phosphopeptides comprising the steps of:
   completely digesting a soluble monovalent cation salt of casein in solution,
   introducing a di or trivalent metal ion to cause aggregation of at least the selected phosphopeptides in said digested solution, and
   diafiltering the digested solution containing the aggregating ion through a filter having a molecular weight exclusion limit selected to retain at least said aggregated phosphopeptides while passing the bulk of the remaining phosphopeptides in a filtrate, wherein the metal ion concentration during diafiltration is maintained at a level effective to maintain the aggregated phosphopeptides in aggregate form.

2. The method of claim 1, wherein the selected phosphopeptides are anticariogenic phosphopeptides and the molecular weight exclusion limit adopted during the filtering step substantially falls within the range 10,000 to 20,000.

3. The method of claim 1, wherein the soluble monovalent cation salt of casein is present in the solution in a concentration substantially falling within the range 0.1 to 50% w/w.

4. The method of any one of claim 1 wherein the digestion step is performed using a proteolytic enzyme and the ratio of proteolytic enzyme to soluble monovalent cation salt of casein in the solution falls substantially within the range 1:1000 to 1:10 (w:w) selected to allow complete digestion of the casein salt.

5. The method of claim 1, wherein the pH and the temperature of the solution is controlled to allow complete digestion of the casein salt.

6. The method of claim 5, wherein the temperature of the solution lies substantially within the range 20° C. to 60° C.

7. A method for the preparation of selected phosphopeptides having anticariogenic and other activities, comprising the steps of:
   completely digesting a soluble monovalent cation salt of casein in solution with a proteolytic enzyme,
   adding a mineral acid to the solution to adjust the pH to about 4.7,
   removing any precipitate produced,
   adding $CaCl_2$ to the digested solution to a level of about 1.0% w/v to cause aggregation of at least the selected phosphopeptides in said digested solution, and
   separating the aggregated phosphopeptides from the solution by filtration including diafiltration with the $CaCl_2$ containing solution through a filter having a molecular weight exclusion limit lying substantially within the range 10,000 to 20,000 while passing the bulk of the remaining phosphopeptides and non-phosphorylated peptides and solution in a filtrate, wherein the metal ion concentration during diafiltration is maintained at a level effective to maintain the aggregated phosphopeptides in aggregate form.

8. The method of claim 1, wherein the soluble monovalent cation salt of casein is selected from sodium caseinate and potassium caseinate.

9. The method of claim 7, wherein the proteolytic enzyme is selected from pancreatin, trypsin, papain, chymotrypsin and mixtures thereof.

10. Phosphopeptides when produced by the method of claim 1.

11. The filtrate of the method of claim 1.

12. The method of claim 1, wherein the diafiltering step further comprises diafiltering the digested solution with one or more volumes of a solution of the metal ion.

13. The method of claim 12, wherein the metal ion is selected from the group consisting of calcium, iron, and zinc.

14. The method of claim 13, further comprising, after the digesting step, the steps of:
   acidifying the digested solution to produce a precipitate,
   then centrifuging the digested solution to produce a supernatant,
   then removing the precipitate,
   then microfiltering the supernatant, and
   then adding the metal ion to the supernatant.

15. The method of claim 14, wherein the metal ion is a calcium ion produced by addition of $CaCl_2$ to the digested solution, and the diafiltering step further comprises diafiltering the $CaCl_2$-containing solution through a filter having a molecular weight exclusion limit lying substantially within the range of 10,000 to 20,000 while passing the bulk of the remaining phosphopeptides and non-phosphorylated peptides and solution in the filtrate.

16. The method of claim 7, wherein the diafiltering step further comprises diafiltering the digested solution with one or more volumes of a solution of the metal ion.

17. An anticariogenic composition consisting essentially of phosphopeptides prepared by the method of claim 1, wherein the composition is substantially free of phosphopeptides having a molecular weight of less than about 10,000.

18. An anticariogenic composition consisting essentially of anticariogenically active phosphopeptides prepared by the method of claim 13.

\* \* \* \* \*